United States Patent

Kesling

[11] 4,120,090
[45] Oct. 17, 1978

[54] ORTHODONTIC BAND WITH IDENTIFICATION AND METHOD OF MAKING THE IDENTIFICATION

[76] Inventor: Peter C. Kesling, Green Acres, LaPorte, Ind. 46350

[21] Appl. No.: 777,667

[22] Filed: Mar. 15, 1977

Related U.S. Application Data

[63] Continuation-in-part of Ser. No. 628,332, Nov. 3, 1975, abandoned.

[51] Int. Cl.$^2$ ............................................. A61C 13/22
[52] U.S. Cl. ................................... 32/14 A; 427/287
[58] Field of Search ............... 32/14 A; 40/21; 427/2, 427/265, 287

[56] References Cited

U.S. PATENT DOCUMENTS

| | | | |
|---|---|---|---|
| 1,646,565 | 10/1927 | Vaughn | 427/287 |
| 2,119,546 | 7/1938 | Knugg | 427/287 |

OTHER PUBLICATIONS

ORMCO Corporation, Catalog 11, May 19, 1964, 1332 So. Lone Hill Rd., Glendora, Calif.

*Primary Examiner*—Robert Peshock
*Attorney, Agent, or Firm*—Lloyd L. Zickert

[57] ABSTRACT

An orthodontic band having identifying means which includes a first coating or layer of material in the form of a suitable geometrical shape and a second coating or layer of material on the first coating in the form of indicia. The orthodontic band is preformed and of stainless steel with a highly polished exterior surface. The identifying means is applied by first applying a coating of material onto the exterior surface of the band and then curing that material. Thereafter a second coating of material which is substantially opaque is applied over the first coating and in the form of indicia. The second coating is thereafter cured.

1 Claim, 5 Drawing Figures

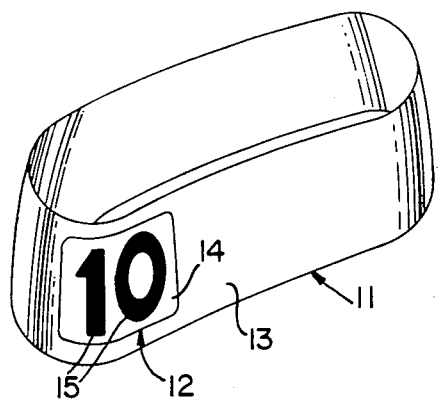
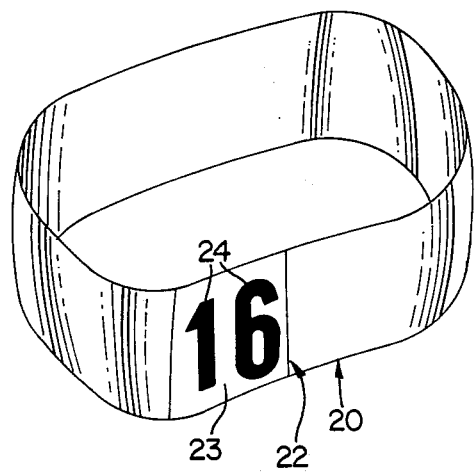
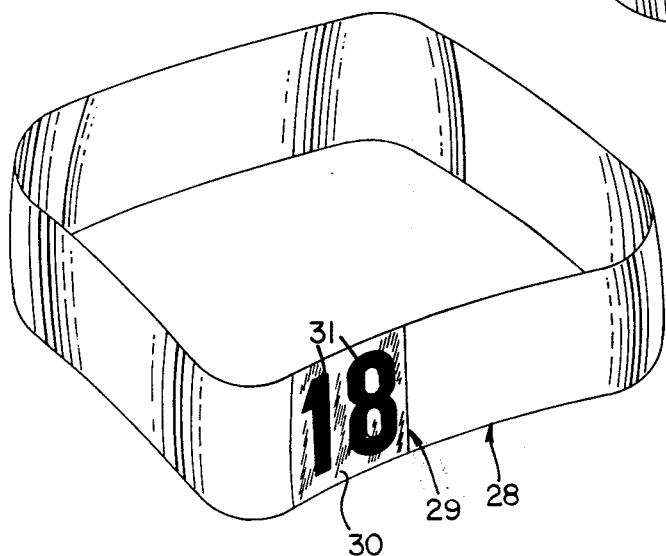
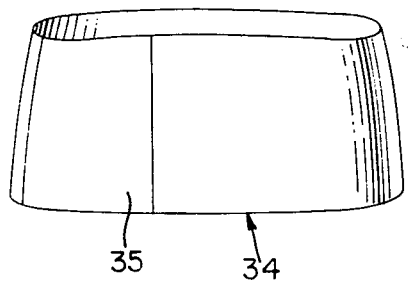
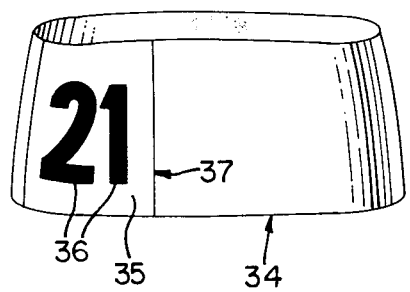

ORTHODONTIC BAND WITH IDENTIFICATION AND METHOD OF MAKING THE IDENTIFICATION

This application is a continuation-in-part of my co-pending application Ser. No. D-628,332, filed Nov. 3, 1975 and now abandoned.

This invention relates in general to preformed orthodontic bands, and more particularly to preformed orthodontic bands having easy-to-read identification on their exterior surface, and still more particularly to a method for applying the easy-to-read identification.

It has been well known to use preformed orthodontic bands in the practice of orthodontia. These bands are provided in various sizes and shapes in order to meet the needs of the orthodontist who would fit the bands to the patient during the installation of appliances. The bands serve to mount appliances and/or attachments onto the teeth of a patient. The appliances are welded, soldered, or cemented to the bands. Inasmuch as the bands come in so many different sizes and shapes, it is necessary to provide identifying means on the bands to facilitate use by the orthodontist. The bands are of stainless steel with highly polished exterior surfaces, which makes it difficult to apply identification. Heretofore, such identification has been applied by printing or stamping of indicia such as numerals and/or letters onto the exterior surface of the bands. Such indicia applied directly to the surface is oftentimes difficult to read and may be removed during handling. When the indicia is removed it becomes very difficult to identify a band and it becomes useless.

It is also well known that bands heretofore provided with indicia for identification have often lost the advantage of the indicia through handling and/or cold sterilizing when it may be removed or rendered illegible. Such sterilizing involves the immersion of the bands into a sterilizing solution at room temperature and may become necessary when a band is tried on the tooth of a patient and found to be of the wrong size. It must be sterilized for further usage as it is too costly to throw away.

Heretofore, it has also been known to provide identification by applying pressure-sensitive labels to bands. However, such labels are also easily removable during handling and also during cold sterilizing, thereby making the identification of marginal use. Further, no such pressure-sensitive labels have been known that can withstand the normal uses put to bands.

It is therefore an object of the present invention to overcome the difficulties heretofore encountered in providing identification for preformed orthodontic bands and to provide a unique method of making easy-to-read identification on orthodontic bands and to provide preformed orthodontic bands having long lasting, easy-to-read identification.

It is a further object of this invention to provide a method for applying identification to preformed orthodontic bands having highly polished exterior surfaces wherein the method includes the application of a first coating or layer of material and thereafter the application of a second layer or coating of material onto the first layer in the form of indicia for defining identification.

The method of applying easy-to-read identification onto preformed stainless steel orthodontic bands having highly polished exterior surfaces according to the invention includes the application such as by printing of a non-toxic Federal Drug Administration (FDA) approved material onto the exterior surface of the band in the form of a suitable geometrical shape. For example, the first layer may be sized to receive indicia thereon and may be in the form of a rectangle or the like. The material would be of a suitable ink or paint which will dry or cure in a suitable manner. Thereafter a second layer or coating of material is applied onto the first coating and in the form of indicia and it thereafter would be cured in a suitable manner.

The combination of the first and second coatings thereby defines the identification for the band. The first layer defines a background onto which the second layer in the form of indicia can be easily read. The first layer is in the form of a continuous sheet which will have good adhesion characteristics to the highly polished surface of the band. Moreover, the first layer will be of a material which will at least visually dull the surface of the band. In this respect, it may be of a transluscent character. Preferably it will be of an opaque character and a color suitable for the background of the indicia coating placed thereon. The second coating in the form of indicia would be of a substantially opaque nature and of a color that would contrast with the color of the first coating.

It has been found that identification of this unique nature has excellent lasting qualities for the use put to the bands. More specifically, the identification of the invention will withstand the usual handlings occasioned by the orthodontist and/or any assistant as well as any necessary cold sterilization process.

Another object of this invention is in the provision of identification for preformed orthodontic bands having highly polished exterior surfaces which will be long lasting and which can withstand cold sterilization.

Other objects, features and advantages of the invention will be apparent from the following detailed disclosure, taken in conjunction with the accompanying sheet of drawings, wherein like reference numerals refer to like parts, in which:

FIG. 1 is a perspective view of a preformed orthodontic band having one form of identification thereon according to the present invention;

FIG. 2 is a perspective view of an orthodontic band of a different shape from that in FIG. 1 and which has a modified form of identification thereon according to the present invention;

FIG. 3 is a perspective view of an orthodontic band of a still different shape from that shown in FIGS. 1 and 2 and having a still further modified form of identification thereon;

FIG. 4 is an elevational view of an orthodontic band like that in FIG. 1 and illustrating the condition of the band following the application of the first coating of the identification means; and FIG. 5 is a view similar to FIG. 4 and showing a further step accomplished in the application of the second coating onto the first coating in the form of indicia to complete the formation of the identification means.

Referring now to the drawings and particularly to FIG. 1, a preformed orthodontic band 11 is illustrated with identification 12 applied to the exterior surface 13 at an area near one corner of the band. It will be appreciated that the preformed band 11 is of a particular size and shape so that it would be suitable for use on a particular tooth of such a size as to provide a snug fit between the band and the tooth.

The preformed bands are made by suitable metal-forming procedures from stainless steel and thereafter subjected to a suitable polishing operation so that the surfaces of the bands are ultimately highly polished and smooth. One such polishing procedure is called "harperizing" which comprises agitating the bands in a suitable polishing material or compound in a well known manner. Following removal of the bands from the polishing material, they are washed to remove the polishing material thereby conditioning them for having identification applied in a suitable manner.

Accordingly, identification 12 is applied to a highly polished and metallic surface. Preferably the identification is applied at an area which will not show when the band is cemented to a tooth in the mouth. Further the identification is applied to an area where it will not interfere with the attachment of any appliances to the band. The identification 12 is located on the lingual side of the band which would not show when mounted on a tooth of a patient. Further the identification is located at one end of the lingual side so as not to interfere with the possible attachment to the lingual side of a lingual button or other appliance.

Identification 12 in FIG. 1 includes a first coating or layer 14 of non-toxic FDA approved material such as a suitable ink or paint; and a second layer or coating 15 of non-toxic FDA approved material and in the form of indicia, and in this illustration the numeral "10." It can be appreciated that the first coating 14, while shown to be of rectangular geometrical shape, could be of any desired geometrical shape to provide a suitable background for the indicia coating 15. Further the first coating 14 in the form of a rectangular shape has its top and bottom edges spaced from the top and bottom edges of the band although the shape may run to the edges as in the embodiments of FIGS. 2, 3 and 5. If desired, the geometrical shape of the first coating 14 could be oval, triangular, or of any suitable shape so long as it provides a background for the indicia coating 15. In this respect the coating 14 may be termed a background coating.

The coating 14 is essentially opaque as is the coating 15 and the coatings are preferably of contrasting colors.

FIG. 2 illustrates a band 20 of a different shape from the band 11 and which is provided with an identification 22 that differs from the identification 12 in that the first layer or coating of material 23 extends the full width of the band from the top to the bottom edges. The indicia coating 24 is applied to the background coating 23 and represents the numeral "16." The coatings 23 and 24 are essentially opaque and of contrasting colors as in identification 12 of the embodiment of FIG. 1. The identification is located on the lingual side of the band and at one end of the lingual side so as to avoid interference with the welding of any attachments onto the lingual side. The embodiment of FIG. 3 differs from the embodiment of FIG. 2 wherein a band 28 having identification 29 is illustrated. The band 28 is of a different shape from the band 20 and of different shape from the band 11. Identification 29 differs only in that the first or background coating 30 is of a translucent nature rather than opaque. The transluscent coating 30 is such that it will visually dull the highly polished exterior surface of the band so that the indicia coating 31 will readily stand out on the background coating. Otherwise the coating 30 will also be of a non-toxic FDA approved material and one onto which the indicia coating will readily adhere. It is only necessary to dull the highly polished surface in order to render the indicia coating easily readable.

The method of the invention in making an easy-to-read identification for a stainless steel preformed orthodontic band having a highly polished exterior surface is illustrated in FIGS. 4 and 5 wherein the band is designated by the numeral 34. The first or background coating or layer 35 is initially applied to the exterior surface of the band. As already mentioned, this coating will be of a material that is in the form of an ink or paint which may be easily applied by machine or manually.

One specific form of applying the coating would be by using a printing apparatus which would print the coating onto the band. It should also be appreciated that the coating could be sprayed onto the surface of the band. Following the application of the coating, it is suitably cured. One form of material requires heat curing wherein the band and coating is subjected to a temperature of about 300° F. for about 15 minutes. Following the curing of the background coating 35, the indicia coating 36 is applied onto the background coating by machine or manually. Again the indicia coating may be printed onto the cured background coating after which the indicia coating is cured in a suitable manner such as by heat curing as above explained. After the indicia coating is cured the completed identification 37 is accomplished for the band 34 and the band then may be packaged for shipment.

It will therefore be appreciated that the identification for orthodontic bands according to the present invention and the method of making the identification provides a long lasting identification on a band which can withstand known usage and maintain its integrity for the benefit of the orthodontist. Such long lasting identification will eliminate the need to dispose of unidentified bands and render the use of the bands more efficient.

It will be understood that modifications and variations may be effected without departing from the scope of the novel concepts of the present invention, but it is understood that this application is to be limited only by the scope of the appended claims.

The invention is hereby claimed as follows:

1. The method of making easy-to-read identification for a stainless steel preformed orthodontic band having a highly polished exterior surface, comprising the steps of applying a first coating of non-toxic material of one color onto the exterior surface and over substantially the entire width of the band at one area along the band which at least visually dulls the polished surface, and applying a second coating of non-toxic substantially opaque material of a contrasting color onto and over substantially the entire surface of said first coating in the form of a selected indicia to permit easy identification of the band type and/or size, said steps of applying said coatings including printing of the first coating onto the band, curing the coating by subjecting it to about 300° F. for about 15 minutes, printing of the second coating onto the cured first coating, and curing the second coating by subjecting it to about 300° F. for about 15 minutes.

* * * * *